United States Patent [19]

Matolcsy et al.

[11] 4,200,650

[45] Apr. 29, 1980

[54] 2-AMINO-CYCLOPENT-1-ENE-1-THIOCARBOXYLIC ACID-DISULFIDES TO TREAT NORADRENERGIC MALFUNCTIONS

[75] Inventors: György Matolcsy; Piroska Bartók nee Berencsy, both of Budapest; Bélá Kiss, Vecses; Eva Palosi, Budapest; Egon Kárpati, Budapest; Laszló Szporny, Budapest, all of Hungary

[73] Assignee: Richter Gedeon Vegyészeti Gyár Rt., Budapest, Hungary

[21] Appl. No.: 6,523

[22] Filed: Jan. 25, 1979

Related U.S. Application Data

[62] Division of Ser. No. 865,429, Dec. 29, 1977.

[30] Foreign Application Priority Data

Dec. 30, 1976 [HU] Hungary ................................ RI 610

[51] Int. Cl.² ........................................... A61K 31/195
[52] U.S. Cl. ................................................. 424/319
[58] Field of Search ......................................... 424/319

Primary Examiner—Stanley J. Friedman
Attorney, Agent, or Firm—Karl F. Ross

[57] ABSTRACT

New 2-amino-cyclopent-1-ene-thiocarboxylic acid-disulfides of the general formula (I),

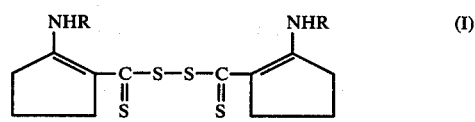

wherein R is hydrogen, a $C_{1-6}$ alkyl group having optionally a $C_{1-4}$ alkoxy, hydroxy, carboxy and/or amino substituent, a $C_{2-4}$ alkenyl group, a $C_{3-8}$ cycloalkyl group or phenyl group, are prepared by oxidizing the respective 2-amino-cyclopent-1-ene-dithiocarboxylic acids of the general formula (II),

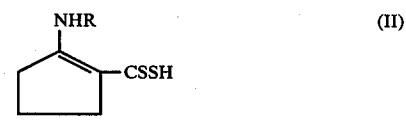

wherein R is as defined above.

The new compounds of the general formula (I) and their salts exert dopamine-$\beta$-hydroxylase inhibiting effects and can be applied in the therapy.

7 Claims, No Drawings

2-AMINO-CYCLOPENT-1-ENE-1-THIOCARBOXYLIC ACID-DISULFIDES TO TREAT NORADRENERGIC MALFUNCTIONS

This is a division of application Ser. No. 865,429, filed Dec. 29, 1977.

This invention relates to new 2-amino-cyclopent-1-ene-1-thiocarboxylic acid-disulfides and pharmaceutical compositions containing the same, furthermore to a process for the preparation thereof.

The novel compounds according to the invention correspond to the general formula (I),

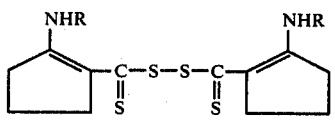

wherein R is hydrogen, a $C_{1-6}$ alkyl group having optionally a $C_{1-4}$ alkoxy, hydroxy, carboxy and/or amino substituent, a $C_{2-4}$ alkenyl group, a $C_{3-8}$ cycloalkyl group or phenyl group. Salts of the above compounds are also within the scope of the invention.

These compounds exert dopamine-β-hydroxylase inhibiting effects.

As known, substances influencing nervous functions exert their activities almost exclusively on the level of the stimulus transfer processes. These processes are relatively known, thus it is possible to prepare compounds by which such processes can be influenced in a more or less controlled manner. The intervention into elementary nervous processes involves, however, not only the influencing of the nervous system itself, but also influencing the processes being under the control of the nervous system. The efforts made in this respect in the last few years also encompass the research work performed in connection with dopamine-β-hydroxylase and compounds inhibiting its effects.

Dopamine-β-hydroxylase catalyzes the conversion of dopamine into noradrenaline, which is the last enzymatic step of the biosynthesis of noradrenaline. The normal level of noradrenaline, a substance playing a significant role in the transport processes of symphatic nervous stimuli, is an essential factor with respect to the normal nervous functions and to the normal functions of processes being under the control of the nervous system. Substances with dopamine-β-hydroxylase inhibiting effects enable one to influence the noradrenergic functions. This fact is of great importance with respect of both research work and therapy, since, in the field of research work, the consequences of the partial or total extinction of noradrenergic functions can be examined by decreasing the noradrenaline level with dopamine-β-hydroxylase inhibitors, and, in the field of therapy, the hyperfunction of the noradrenergic system can be compensated with dopamine-β-hydroxylase inhibitors. To our recent knowledge dopamine-β-hydroxylase inhibitors can be applied in the therapy of hypertension and Parkinsonism.

As known, benzyloxyamine and benzylhydrazine exert dopamine-β-hydroxylase inhibiting effects (van der Schoot et al.: Advances in Drug Research, Vol. 2, p. 47, Harper and Simmons; Nikodijevic et al.: J. Pharm. Exp. Ther. 140, 224/1963/). These compounds however, exert their activities for a short period, thus they are not applied in the therapy. Disulfiram and diethyl dithiocarbamate, the reduction metabolite of the former compound (Goldstein et al.: Life Sci. 3, 763/1964/), furthermore several N,N-disubstituted dithiocarbamates (Maj et al.: Eur. J. Pharmacol. 9, 183/1970/; Lippman et al.: Arch. Int. Pharmacodyn. Ther. 189, 348/1971/) are substances known to exert strong dopamine-β-hydroxylase inhibiting effects. 2,2-Dipyridyl proved to be also effective under in vitro conditions (Green: Biochim. Biophys. Acta 81, 394/1964/). Bis(1-methyl-4-homopiperazinyl-thiocarbonyl)- disulfide is one of the most potent dopamine-β-hydroxylase inhibitors under in vivo conditions (Florvall et al.: Acta Pharmaceut. Sulcica 7, 7/1970/). Aromatic and alkyl thiourea derivatives exert long-lasting dopamine-β-hydroxylase inhibiting effects (Johnson et al.: J. Pharm. Exptl. Ther. 171, 80/1970/).

Of the microbial substances fusaric acid (5-butylpicolinic acid) and its derivatives (Hidaka et al.: Molec. Pharmacol. 9, 172/1973/), oosponol (Umezawa et al.: J. Antibiotics 25, 239/1972/) and dopastine (Iinuma et al.: J. Arg. Biol. Chem. 38, 2107/1974/) are known to exert strong dopamine-β-hydroxylase inhibiting effects.

Subsequent examinations have shown that some of the known and commercially available drugs, such as hydralazine, methimazol and amphetamine, also possess dopamine-β-hydroxylase inhibiting effects.

Most of the above compounds have, however, the disadvantage that although they possess dopamine-β-hydroxylase inhibiting effects, they are rather toxic in prolonged treatments, thus they can be applied in the therapy in a restricted manner, if at all.

The new compounds according to the invention possess strong dopamine-β-hydroxylase inhibiting effects and are less toxic than the known compounds with similar activities. Consequently the new compounds can be applied to great advantage in the therapy.

The dopamine-β-hydroxylase inhibiting effects of the new compounds according to the invention were examined by the following tests:

The tests were performed on male Wistar rats weighing 150 to 200 g. The dopamine-β-hydroxylase inhibiting effects of the compounds were evaluated by determining the change of noradrenaline, dopamine and adrenaline levels of the cerebrum, heart, spleen and adrenal gland. The serotonine and 5-hydroxy-indolylacetic acid levels of the cerebrum were also determined. The measurements were performed as follows:

The animals were decapitated, the cerebrum, heart, spleen and adrenal gland were removed quickly, and the organs were frozen by placing them onto a metal sheet cooled with dry ice. The frozen organs were stored for maximum one night at −20° C.

Determination of the adrenaline content of adrenal gland

The adrenal glands were freed from fat and homogenized in 3.0 ml of ice-cold 0.4 n perchloric acid. The homogenized mixtures were centrifuged for 10 minutes at 0° C. with a speed of 3200 r.p.m. using a Janetzky K-70 type centrifuge. 0.05 ml samples were taken from the supernatant, and the adrenaline level was determined directly by the method of Laverty et al. (Anal. Biochem. 22, 269/1968/).

Determination of the noradrenaline content of heart and spleen

The organs were weighed in frozen state and then homogenized in 5.0 ml of 0.4 n perchloric acid containing 0.05% of EDTA-Na$_a$ and 0.1% of Na$_2$S$_2$O$_5$. The homogenized mixtures were centrifuged as described above for the treatment of adrenal gland, the supernatants were decanted, and the pH was adjusted to 8.0±0.1 with a 0.1 molar tris buffer containing 20 g/l of NaOH and 25 g/l of EDTA-Na$_2$. 100 mg of prepared Al$_2$O$_3$ (Anton et al.: J. Pharm. Ther. 138, 360/1962/) were added to the samples, and the mixtures were shaken mechanically for 20 minutes. Thereafter Al$_2$O$_3$ was washed with 2×10 ml of distilled water, and noradrenaline was eluted with 1.0 ml of 0.05 n perchloric acid. 0.5 ml samples of the eluate were applied for the determination of noradrenaline. Noradrenaline was determined according to the method of Shellenberger et al. (Anal. Biochem. 39, 356/1971/), with the following modifications of the basic procedure: 0.5 ml of 0.1 molar Na-K-phosphate buffer, containing 9 g/l of EDTA-Na$_2$, were added to 0.5 ml of the eluate, and the catecholamines (noradrenaline in the examination of heart and spleen and noradrenaline and dopamine in the examination of the cerebrum) were oxidized with 0.1 ml of a 0.1 n iodine solution in 5% potassium iodide. After exactly 2 minutes oxidation was stopped by adding 0.25 ml of a 2.5% sodium sulfite solution in 4.4 n aqueous sodium hydroxide to the mixture. 2 minutes after the introduction of the alkaline sulfite solution 0.2 ml of concentrated acetic acid were added to the samples, upon which the pH decreased to 4.4 to 4.5 Thereafter the samples were placed for 5 minutes into a drying oven heated to 100° C., and then the samples were cooled with ice water. The fluorescency of noradrenaline was measured with an OPTON spectrophotometer at wavelengths of 380 nm (excitation) and 490 nm (emission).

Determination of the noradrenaline, dopamine, serotonine and 5-hydroxy-indolylacetic acid contents of brain The brains were homogenized in 10 parts by volume of 0.4 n perchloric acid. The homogenized mixture was stored at −20° C. overnight, thereafter it was thawed and centrifuged as described above. A sample of the homogenized mixture corresponding to 0.5 g of brain was removed, the pH of the sample was adjusted to 8.0±0.1 with 0.1 molar tris-buffer of the above composition, and the sample was processed as described above for the determination of the noradrenaline content of heart and spleen, with the difference that 1.5 ml of 0.05 n perchloric acid were applied as eluting agent. 0.5 ml of the eluate were applied to determine the noradrenaline and dopamine contents. The measurement was performed as described above, with the difference that samples of 0.5 ml were applied for the recording of the fluorescency of noradrenaline. The residua was placed for 50 minutes into a drying oven heated to 100° C., thereafter the sample was cooled with ice water, and the fluorescency of dopamine was recorded at wavelengths of 325 nm (excitation) and 380 nm (emission).

In a further test series the serotonine and 5-hydroxyindolylacetic acid contents were also determined, beside the determination of the noradrenaline and dopamine content, from the same sample. In this instance the brains were homogenized in 10 ml of 75% ethanol, 0.2 ml of EDTA-Na$_2$ and 5% of ascorbic acid were added to the homogenized mixtures, and the homogenized mixtures were maintained at −20° C. overnight. The mixtures were centrifuged as described above, and 5.0 ml samples of the supernatant were removed. The samples were diluted with equal volumes of distilled water, and poured onto ion exchange columns of 0.5×1.5 cm dimensions, filled with buffered Amberlite CG-30 (200 to 400 mesh). The columns were washed with 5 ml of distilled water followed by 1.0 ml of 0.2 n hydrochloric acid, and the first effluent and the aqueous wash were collected for the determination of 5-hydroxy-indolylacetic acid. Elution was continued with further 1.2 ml of 0.2 n hydrochloric acid in order to remove noradrenaline, dopamine and serotonine. Samples of 0.3 ml were used for the determinations.

Noradrenaline and dopamine were determined by the method of Shellenberger, modified as described above, whereas serotonine was determined by the method of Curzon et al. (Brit. J. Pharmacol. 39, 653/1970/). The basic method was modified as follows: A 0.5% solution of ortho-phthal(di)aldehyde in absolute ethanol was diluted with 10 n hydrochloric acid to 50-fold of its original volume, and 0.6 ml of the resulting 0.01% ortho-phthal(di)aldehyde solution were added immediately to 0.5 ml of the serotonine-containing sample. The sample was placed into a hot water bath for 10 minutes, thereafter cooled with tap water, and the fluorescency was recorded at wavelengths of 360 nm (excitation) and 490 nm (emission).

5-Hydroxy-indolylacetic acid was determined from the mixture of the first effluent and the aqueous wash. 10 ml of distilled water and 0.2 ml of concentrated hydrochloric acid were added to the mixture, and the sample was poured onto a 0.8×4.0 cm column filled with Sephadex G-10. The column was washed with 15 ml of 0.1 n hydrochloric acid followed by 1.8 to 2.0 ml of 0.02 n aqueous ammonia, and then 5-hydroxyindolylacetic acid was eluted with further 2.0 ml of aqueous ammonia. 0.5 ml samples were used in the measurements, and the determination was performed according to the method of Korf et al. (Biochem. Pharmacol. 20, 659/1971/).

The test results are summarized in Table 1. In the tests disulfiram, 2,2-dipyridyl, bis(1-methyl-4-homopiperazinyl-thriocaronyl)-disulfide, sodium diethyldithiocarbamate and N-phenyl-N'-(2-thiazolyl)-thiourea were applied as reference substances. The values indicated in Table 1 are the percentages in relation to the amine levels of the controls measured in the same tests (± standard error). The statistical calculations were performed on a TPA/i type computer, using Student's t test.

The meanings of the abbreviations used in Table 1 are as follows:
NA: noradrenaline;
DA: dopamine;
SE: serotonine;
5-HIAA: 5-hydroxy-indolylacetic acid;
AD: adrenaline;
Comp.: compound;
Adm.: method of administration;
Dos. dosage, mg/kg;
Time: period of treatment, hours;
a: $0.01 < p < 0.05$;
b: $0.001 < p < 0.01$;
d: $p < 0.001$;
M-1: 2-amino-cyclopent-1-ene-thiocarboxylic acid disulfide;
M-2: 2-(N-butyl)-amino-cyclopent-1-ene-thiocarboxylic aciddisulfide;
M-3: 2-(N-butyl)-amino-cyclopent-1-ene-thiocarboxylic acid-disulfide(zinc salt);

M-4: 2-(N-methoxyethyl)-amino-cyclopent-1-ene-thiocarboxylic acid disulfide;

M-5: 2-(N-cyclohexyl)-amino-cyclopent-1-ene-thiocarboxylic acid disulfide;

M-6: 2-(N-ethyl)-amino-cyclopent-1-ene-thiocarboxylic acid-disulfide;

M-7: 2-(N-allyl)-amino-cyclopent-1-ene-thiocarboxylic acid-disulfide;

DS: disulfiram[bis(diethylthiocarbamoyl)-disulfide];

DDC-Na: sodium diethyldithiocarbamate;

2,2-D: 2,2-dipyridyl;

FLA-63: bis(1-methyl-4-homopiperazinyl)-thiocarbonyl-disulfide;

U-14624: N-phenyl-N'-(2-thiazolyl)-thiourea;

n = number of animals.

catecholamine level cannot be observed in these organs with known dopamine-$\beta$-hydroxylase inhibitors, either.

The toxicity date of the compounds according to the invention are listed in Table 2.

Table 2

| Compound | Animal | Method of administration | LD$_{50}$ mg/kg |
|---|---|---|---|
| M-1 | mice | i.p. | ~800 |
| M-3 | mice | i.p. | ~450 |
| M-4 | mice | i.p. | >1500 |
| M-5 | mice | i.p. | >1000 |
| M-6 | mice | i.p. | 1000-1500 |
| M-7 | mice | i.p. | >1000 |
| FLA-63 | mice | i.p. | 150 |
| 2,2-D | mice | i.p. | 280 |
|  | rats | i.p. | ~150 |

Table 1

| | | | | | Amine levels /percentages in relation to the controls/ | | | | | |
|---|---|---|---|---|---|---|---|---|---|---|
| | | | | | Brain | | | | Heart | Spleen | Adrenal gland |
| Comp. | Adm. | Dos. | Time | n | NA | DA | SE | 5-HIAA | NA | NA | AD. |
| M-1 | i.p. | 100 | 4 | 6 | 69.5±12.1[b] | 121.2±5.8[a] | — | — | 86.5±3.7[a] | — | 87.2±6.7 |
|  | i.p. | 200 | 4 | 6 | 56.7±5.9[c] | 124.5±1.9[c] | 114.6±4.7[a] | 152.5±18.8[a] | 82.5±5.4 | 92.6±12.4 | 70.9±5.8[c] |
|  | i.p. | 200 | 8 | 6 | 56.5±6.3[c] | 109.0±5.9 | 110.7±5.1 | 125.3±10.7 | 83.2±9.5 | 91.2±12.6 | 60.2±3.2[c] |
| M-2 | i.p. | 100 | 4 | 17 | 80.1±4.3[a] | 118.3±5.7[a] | — | — | 91.5±5.2 | — | 81.0±8.5[a] |
|  | i.p. | 200 | 4 | 6 | 70.9±5.2[c] | 94.2±7.5 | 97.6±5.6 | 127.8±8.3[a] | 108.5±9.4 | 114.5±28.2 | 91.7±4.3 |
|  | i.p. | 200 | 8 | 6 | 81.6±7.3 | 91.0±12.7 | 97.3±11.3 | 126.4±7.1[a] | 91.7±4.6 | 96.4±23.1 | 87.7±4.2 |
| M-3 | i.p. | 50 | 4 | 6 | 85.0±7.1 | 112.2±12.0 | — | — | 84.5±4.1 | — | 66.3±5.5[c] |
|  | i.p. | 100 | 4 | 13 | 73.5±3.2[c] | 121.3±6.1[a] | — | — | 91.5±8.1 | — | 60.5±3.6[c] |
|  | p.o. | 500 | 4 | 6 | 98.8±2.5 | 99.2±5.0 | — | — | 108.8±3.2 | — | 100.3±8.3 |
| M-4 | i.p. | 100 | 4 | 6 | 41.9±2.7[c] | 131.5±8.9[b] | 113.3±2.8[a] | 108.3±9.6 | 91.8±5.9 | 81.4±10.8 | 77.5±6.3[a] |
|  | i.p. | 200 | 4 | 6 | 39.6±4.9[c] | 134.6±4.0[c] | 112.8±5.6 | 150.9±15.4[c] | 91.7±9.2 | 69.9±16.9 | 96.3±6.7 |
|  | i.p. | 200 | 8 | 6 | 28.5±1.4[c] | 120.6±5.8[a] | 106.0±7.5 | 161.4±10.0[c] | 75.7±3.7[a] | 61.9±9.9 | 97.0±7.9 |
|  | p.o. | 500 | 4 | 5 | 73.6±2.8[a] | 114.5±2.4[b] | 102.7±5.3 | 95.4±6.0 | 86.3±10.1 | 103.1±18.9 | 96.3±6.0 |
|  | p.o. | 500 | 8 | 5 | 51.2±2.8[c] | 111.0±4.0 | 90.9±6.7 | 105.9±4.9 | 74.0±8.4[a] | 101.0±14.3 | 88.1±5.1 |
| M-5 | i.p. | 200 | 4 | 6 | 64.6±1.8[c] | 124.2±4.0[a] | 104.5±7.6 | 142.8±8.0[c] | 94.7±6.8 | 83.2±8.9 | 109.0±2.3 |
|  | i.p. | 200 | 8 | 6 | 76.9±2.2[c] | 116.2±3.3[b] | 105.3±4.5 | 177.5±10.8[c] | 89.5±3.0 | 68.7±6.7 | 105.6±3.3 |
| M-6 | i.p. | 100 | 4 | 5 | 41.8±2.3[c] | 99.0±5.22 | 106.7±2.2 | — | 92.9±3.3 | 64.1±7.6 | 123.4±4.6 |
|  | i.p. | 200 | 4 | 6 | 34.4±2.6[c] | 134.9±5.4[c] | 112.5±5.2 | 155.0±8.5[c] | 97.8±8.8 | 85.0±10.8 | 97.3±4.1 |
|  | i.p. | 200 | 8 | 6 | 34.2±3.5[c] | 121.7±6.1 | 103.9±7.4 | 195.4±4.8[c] | 81.3±5.7 | 86.5±23.5 | 79.0±3.9[c] |
|  | p.o. | 500 | 4 | 5 | 83.9±4.8[a] | 106.7±3.4 | 117.5±4.6[b] | — | 82.4±8.2 | 125.4±12.4 | 121.4±13.7 |
|  | p.o. | 500 | 8 | 5 | 73.7±4.7[a] | 92.6±4.0 | 91.2±0.9[b] | — | 97.5±5.6 | 64.6±12.4 | 107.5±8.9 |
| M-7 | i.p. | 200 | 4 | 6 | 50.5±5.2[c] | 123.6±8.1[a] | 112.7±8.0 | 117.1±6.5 | 100.0±3.9 | 66.1±18.1 | 93.3±8.0 |
|  | i.p. | 200 | 8 | 6 | 64.5±4.4[c] | 104.7±5.7 | 108.0±8.0 | 125.7±10.5 | 91.8±3.7 | 88.5±33.9 | 69.8±6.8[a] |
| DS | i.p. | 200 | 4 | | 22.5[c] | 111 | 122 | — | 98 | — | 52[c] |
|  | | 400 | 4 | | 24.1[c] | 112 | 117 | — | 102 | — | 66[c] |
| DDC-Na | i.p. | 400 | | | 64.1[c] | 120 | — | — | | | |
| 2,2-D | i.p. | 37.5 | 4 | | 79.5[b] | 116 | — | — | 104 | 100 | 80[a] |
|  | | 75 | 4 | | 41.2[c] | 95 | 100 | — | 58[b] | — | 63[b] |
| FLA-63 | i.p. | 50 | 4 | | 24.6[o] | 118 | 124[b] | 134[b] | 96 | 58[c] | 43[c] |
| U-14624 | i.p. | 200 | 4 | | 31.6[o] | 121 | 137[b] | 175[c] | 106 | 111 | 72[b] |

The data of Table 1 clearly demonstrate that the new compounds according to the invention considerably decrease the noradrenaline level in the brain. Depending on the dosage, the method of administration and the duration of treatment, the extent of decrease is 50 to 70%. At the same time a considerable (20 to 30%) increase in dopamine level can also be observed. The increase of serotonine level is less significant, the 5-hydroxy-indolylacetic acid level increases, however, occasionally by 50 to 90%.

The noradrenaline levels of heart and spleen, and the adrenaline level of adrenal gland decrease as well, these decreases are, however, not always significant even for compounds strongly decreasing the cerebral noradrenaline level. This phenomenon can be attributed presumably to the fact that the catecholamine turnovers of these organs are slow, furthermore that adrenal gland possesses a relatively great depot of catecholamines (noradrenaline and adrenaline), and the missing noradrenaline contents of spleen and heart are quickly supplemented by circulation. A unequivocal decrease of

| | | | |
|---|---|---|---|
| Hydralazine | mice | i.p. | 83 |
| DS | rats | p.o. | 8600 ± 370 |
|  | rabbits | p.o. | 1800 ± 130 |
| Dopastine | mice | i.p. | 250-500 |
|  |  | i.p. | 460 |
|  |  | p.o. | 750 |
| Fusaric acid | mice | p.o. | 230 ± 25 |
| Chlorofusaric acid | mice | p.o. | 470 ± 85 |
| Oosponol | mice | i.p. | 40 |
|  |  | p.o. | 280 |
| U-14624 | mice | i.p. | ~680 |
|  |  | p.o. | >1000 |

The data of Table 2 indicate that the LD$_{50}$ values of the new compounds according to the invention are very favourable, thus these compounds can be administered for prolonged time.

The new disulfide compounds of the general formula (I) can be prepared, according to the invention, by oxidizing the corresponding 2-amino-cyclopent-1-ene-1-dithiocarboxylic acids of the general formula (II), wherein R is as defined above.

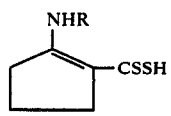

/II/

Oxidation is performed with an oxidizing agent capable of forming disulfides, such as hydrogen peroxide or potassium permanganate.

According to a preferred method of the invention the starting dithiocarboxylic acid is dissolved or suspended in a suitable solvent or diluent, the mixture is rendered alkaline, and then the disulfide is oxidized by adding an acid and hydrogen peroxide to the mixture.

As solvent or diluent preferably water is applied. The reaction mixture is rendered alkaline preferably by adding an alkali hydroxide, such as sodium hydroxide thereto.

The acid applied is preferably a mineral acid, such as sulfuric acid.

The resulting disulfides can be converted, if desired, into their pharmaceutically acceptable salts.

The starting substances are partly known (J. Org. Chem. 37, 1727/1972/). The preparation of the still new substances is described in our co-pending application No.

The invention is elucidated in detail by the aid of the following non-limiting Examples.

EXAMPLE 1

2-(N-Ally;)-amino-cyclopent-1-ene-1-thiocarboxylic acid-disulfide 6.0 g (0.015 moles) of sodium hydroxide are added, as a 10% aqueous solution, to a suspension of 2.98 g (0.015 moles) of 2-(N-allyl)-amino-cyclopent-1-ene-1-dithiocarboxylic acid in 30 ml of water. The mixture is shaken for about 10 minutes. A solution is prepared from 3 ml of water, 0.9 g (0.0075 moles) of concentrated sulfuric acid and 0.9 g (0.0075 moles+10%) of 30% hydrogen peroxide, and this solution is added in portions, at 20° C., to the above alkaline mixture. The reaction mixture is shaken for further 3 hours, thereafter the precipitate is filtered off, washed with water and dried below an I.R. lamp. The title compound, melting at 140°–141° C., is obtained with a yield of 84.4%.

Analysis: Calculated: S: 32.3% N: 7.08%; Found: S: 31.84% N: 6.80%.

EXAMPLE 2

2-(N-Ethyl)-amino-cyclopent-1-ene-1-thiocarboxylic acid-disulfide 12.0 g (0.03 moles) of sodium hydroxide are added, as a 10% aqueous solution, to a suspension of 5.6 g (0.03 moles) of 2-(N-ethyl)-amino-cyclopent-1-ene-1-dithiocarboxylic acid in 60 ml of water. The mixture is shaken for some minutes. A solution is prepared from 8 ml of water, 1.65 g (0.016 moles) of concentrated sulfuric acid and 1.86 g of 30% hydrogen peroxide, and this solution is added in portions, at about 20° C., to the former alkaline solution. The mixture is shaken for additional 3 hours, thereafter the solids are filtered off, washed with water, and dried below an I.R. lamp. The crude product is dissolved in a 1:3 mixture of chloroform and benzene, the solution is decolourized with activated carbon, filtered, and the filtrate is stored in a refrigerator overnight. The separated crystals are filtered off, washed with benzene, and dried in air. The title compound, melting at 150°–152° C., is obtained with a yield of 30%.

Analysis: Calculated: S: 34.4% N: 7.53%; Found: S: 34.1% N: 7.45%.

EXAMPLE 3

2-(N-Methoxyethyl)-amino-1-cyclopent-1-ene-1-thiocarboxylic acid-disulfide 5.0 g (0.0125 moles) of sodium hydroxide are added in portions, as a 10% aqueous solution, to a suspension of 2.7 g (0.0125 moles) of 2-(N-methoxyethyl)-amino-1-cyclopent-1-ene-dithiocarboxylic acid in 27 ml of water at a temperature of about 20° C. The mixture is shaken for some minutes. A solution is prepared from 3 ml of water, 0.66 g (0.0067 moles) of concentrated sulfuric acid and 0.77 g (0.0067 moles) of 30% hydrogen peroxide, and this solution is added to the former alkaline mixture. The reaction mixture is shaken for 3 hours and then allowed to stand overnight. The solids are filtered off, washed with water, and dried below an I.R. lamp. The title compound, melting at 132°–139° C. with decomposition, is obtained with a yield of 28.2%.

Analysis: Calculated: S: 29.65% N: 6.48%; Found: S: 29.18% N: 6.39%.

EXAMPLE 4

2-(N-Cyclohexyl)-amino-cyclopent-1-ene-1-thiocarboxylic acid-disulfide 6.0 g (0.015 moles) of sodium hydroxide are added, as a 10% aqueous solution, to a suspension of 3.6 g (0.015 moles) of 2-(N-cyclohexyl)-amino-cyclopent-1-ene-1-dithiodarboxylic acid in 40 ml of water. The mixture is shaken for 10 minutes. A solution is prepared from 5 ml of water, 0.8 g of concentrated sulfuric acid and 0.9 g of 30% hydrogen peroxide, and this solution is added at about 20° C. to the former alkaline mixture. The reaction mixture is shaken for 4 hours, the solids are filtered off, washed with water, and dried below an I.R. lamp. The title compound, melting at 148°–152° C., is obtained with a yield of 64.6%.

Analysis: Calculated: S: 26.55% N: 5.83%; Found: S: 23.67% N: 5.3%.

What we claim is:

1. A method of treating mammalian noradrenergic malfunctions which comprises administering to affected mammals effective doses of at least one compound of the formula

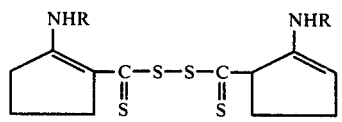

wherein R is hydrogen, $C_{1-6}$ alkyl group unsubstituted or substituted by $C_{1-4}$ alkoxy, hydroxy, carboxy or amino, $C_{2-4}$ alkenyl or, $C_{3-8}$ cycloalkyl.

2. The method according to claim 1 wherein the compound is selected from the group consisting of:
   2-(N-butyl)-amino-cyclopent-1-ene-thiocarboxylic acid-disulfide,
   2-(N-methoxyethyl)-amino-cyclopent-1-ene-thiocarboxylic acid-disulfide,
   2-(N-cyclohexyl)-amino-cyclopent-1-ene-thiocarboxylic acid-disulfide,
   2-(N-ethyl)-amino-cyclopent-1-ene-thiocarboxylic acid-disulfide, and 2-(N-allyl)-amino-cyclopent-1-ene-thiocarboxylic acid-disulfide.

3. The method according to claim 2 wherein the compound is:
2-(N-butyl)-amino-cyclopent-1-ene-thiocarboxylic acid-disulfide.

4. The method according to claim 2 wherein the compound is:
2-(N-methoxyethyl)-amino-cyclopent-1-ene-thiocarboxylic acid-disulfide.

5. The method according to claim 2 wherein the compound is:
2-(N-cyclohexyl)-amino-cyclopent-1-ene-thiocarboxylic acid-disulfide.

6. The method according to claim 2 wherein the compound is:
2-(N-ethyl)-amino-cyclopent-1-ene-thiocarboxylic acid-disulfide.

7. The method according to claim 2 wherein the compound is:
2-(N-allyl)-amino-cyclopent-1-ene-thiocarboxylic acid-disulfide.

* * * * *